(12) United States Patent
Viswanathan et al.

(10) Patent No.: US 11,234,767 B2
(45) Date of Patent: Feb. 1, 2022

(54) METHOD AND APPARATUS FOR AUTOMATED CONTROL AND STEERING OF MULTIPLE MEDICAL DEVICES WITH A SINGLE INTERVENTIONAL REMOTE NAVIGATION SYSTEM

(71) Applicant: STEREOTAXIS, INC., St. Louis, MO (US)

(72) Inventors: Raju R. Viswanathan, St. Louis, MO (US); Walter M. Blume, Webster Groves, MO (US)

(73) Assignee: STEREOTAXIS, INC., St. Louis, MO (US)

( * ) Notice: Subject to any disclaimer, the term of this patent is extended or adjusted under 35 U.S.C. 154(b) by 976 days.

(21) Appl. No.: 14/990,757

(22) Filed: Jan. 7, 2016

(65) Prior Publication Data

US 2016/0192995 A1  Jul. 7, 2016

Related U.S. Application Data

(60) Provisional application No. 62/100,894, filed on Jan. 7, 2015.

(51) Int. Cl.
*A61B 34/20* (2016.01)
*A61B 34/30* (2016.01)
(Continued)

(52) U.S. Cl.
CPC .............. *A61B 34/20* (2016.02); *A61B 5/065* (2013.01); *A61B 5/066* (2013.01); *A61B 34/30* (2016.02);
(Continued)

(58) Field of Classification Search
CPC ............ A61B 34/20; A61B 2034/2046; A61B 2034/2051; A61B 34/25; A61B 34/30; A61B 2034/301; A61B 5/065; A61B 5/066; A61B 2017/00292; A61B 2017/003; A61B 2017/00831; A61B 2017/00876; A61B 2560/0223; A61M 25/01; A61M 25/0105
See application file for complete search history.

(56) References Cited

U.S. PATENT DOCUMENTS 8,721,655 B2    5/2014  Viswanathan et al.
2005/0020911 A1  1/2005  Viswanathan et al.
(Continued)

OTHER PUBLICATIONS

International Preliminary Report on Patentability for PCT/US2016/12546 dated Jul. 11, 2017 pp. 11.
(Continued)

*Primary Examiner* — Ronald Hupczey, Jr.
*Assistant Examiner* — Bradford C. Blaise
(74) *Attorney, Agent, or Firm* — Bryan K. Wheelock

(57) ABSTRACT

Methods are provided for automatically actuating and positioning a first medical device in a subject anatomy with a remote medical navigation system together with a localized second medical device that passes through the first device and is also actuated by the remote navigation system to access a desired target location. After an initial calibration step, an exemplary method comprises:
 (a) determining configurational variables for the first medical device based on a computational model of device deformation and a set of geometrical constraints, and
 (b) automatically steering the first medical device with the remote navigation system to the computationally determined configuration.

10 Claims, 10 Drawing Sheets

(51) Int. Cl.
  *A61B 5/06*    (2006.01)
  *A61B 17/00*   (2006.01)
  *A61B 34/00*   (2016.01)
  *A61B 34/10*   (2016.01)
  *A61B 90/00*   (2016.01)

(52) U.S. Cl.
  CPC ......... *A61B 34/25* (2016.02); *A61B 2017/003* (2013.01); *A61B 2017/00243* (2013.01); *A61B 2017/00876* (2013.01); *A61B 2034/102* (2016.02); *A61B 2034/2051* (2016.02); *A61B 2034/301* (2016.02); *A61B 2090/376* (2016.02); *A61B 2560/0223* (2013.01)

(56) References Cited

U.S. PATENT DOCUMENTS

| | | |
|---|---|---|
| 2008/0091193 A1 | 4/2008 | Kauphusman et al. |
| 2009/0105645 A1 | 4/2009 | Kidd et al. |
| 2010/0298845 A1 | 11/2010 | Kidd et al. |
| 2012/0197100 A1 | 8/2012 | Razavi et al. |
| 2013/0109957 A1 | 5/2013 | 'T Hooft et al. |
| 2013/0172906 A1 | 7/2013 | Olson et al. |
| 2014/0081204 A1 | 3/2014 | Cohen et al. |
| 2015/0157408 A1 | 6/2015 | Viswanathan et al. |

OTHER PUBLICATIONS

International Search Report and Written Opinion for PCT/US2016/12546 dated May 27, 2016 pp. 20.

METHOD AND APPARATUS FOR AUTOMATED CONTROL AND STEERING OF MULTIPLE MEDICAL DEVICES WITH A SINGLE INTERVENTIONAL REMOTE NAVIGATION SYSTEM

CROSS-REFERENCED APPLICATION

This application claims priority to U.S. provisional application Ser. No. 62/100,894 filed on Jan. 7, 2015. The disclosure of the above-referenced application is incorporated herein by reference in its entirety.

FIELD OF THE INVENTION

This invention relates to remotely controlled steering and navigation of medical devices through a subject anatomy with a remote navigation system for interventional medicine, where a first medical device in the form of a remotely steered deflectable sheath is used to assist with the steering of a second medical device in the form of a mapping catheter or an ablation catheter. The second medical device is itself be steered by the same remote navigation system, possibly with a different mode of actuation. More generally, the deflectable sheath could be used as a guide or conduit to place a variety of other medical devices in a desired region of a subject anatomy.

BACKGROUND OF THE INVENTION

In recent years minimally invasive interventional procedures have benefited from the development of remote navigation systems with different forms of actuation that can assist with a variety of minimally invasive interventional medical procedures and permit faster procedures with reduced exposure to X-ray radiation. For instance, a commercial example is the Niobe© magnetic navigation system manufactured by Stereotaxis, Inc. of St. Louis, Mo., USA. This system consists of a set of magnets in a procedure room together with control hardware and software and a user interface; the user interface is available in an adjoining control room for comfortable operation by the user, and the magnetic navigation system is integrated with an X-ray system to receive X-ray image data from the latter. Since this remote navigation system can be operated and controlled from a control room outside the procedure room, X-ray radiation exposure to physicians operating the system is eliminated to a large extent, and the arrangement permits the performance of an interventional medical procedure in most part from outside the procedure room. Procedures are generally faster since the physician can perform the procedure in a more comfortable setting while the device actuation is done by the system, and X-ray exposure to the patient as well is significantly reduced.

Generally, the remote navigation system may be interfaced or integrated with a localization system that determines the spatial location of a medical device within a subject anatomy, permitting the possibility of automatically steering and navigating the medical device to a desired set of target locations using closed loop feedback control. An example of an interventional medical device localization system is the CARTO® Electrophysiology localization system manufactured by Biosense-Webster, Inc. of Diamond Bar, Calif. that localizes various catheter and sheath devices incorporating location sensors and/or electrodes for applications in Electrophysiology. Another example of a localization system is the EnSite NavX™ system manufactured by St. Jude Medical of St. Paul, Minn. The spatial location information can be used for example to direct an ablation catheter device automatically to a series of locations.

Cardiological interventional procedures can benefit greatly from the use of such an integrated system. In the clinical application of interventional cardiac electrophysiology, a catheter-based medical procedure is performed to record electrical activity over the interior (endocardial) heart surface, permitting visualization of electrical activity and any abnormalities or arrhythmias if they exist. Subsequently, a catheter-based ablation procedure (where the ablation catheter is a primary medical device) is performed to ablate and isolate regions of the endocardial surface that function as sources of abnormal electrical activity. This type of procedure can take a long time when performed manually and requires a significant level of skill on the part of the interventional physician. In this context, a remotely operated medical navigation system can offer significant benefits especially if at least a part of the procedure can be efficiently automated, leading to reduced procedure time, reduced X-ray exposure for both physician and patient, and reduced discomfort to physician and patient.

In many cases in Electrophysiology ablation procedures, it is important for the catheter to have a sufficient amount of contact with the endocardial surface. The ablation energy is delivered by means of Radio Frequency (RF) power, and this energy delivery process is optimal when there is good contact between the ablation catheter tip and the endocardiac wall; such a configuration ensures that the RF energy is delivered directly to the tissue surface, with minimal dissipation into the blood pool. Accordingly, various means of measuring contact force have been reported on in the literature. In the context of a remote navigation system, it is useful to have a methodology to ensure that a good level of wall contact is present at the ablation catheter tip. In some cases, certain endocardial locations can be difficult to access depending on the particular subject anatomy. The present invention describes a method and apparatus for ensuring both easier access to a desired target location, and once accessed, applying sufficient contact at the desired target location.

While the literature and art in the area of RF catheter ablation discusses methods to measure contact force, there is an unmet need for generally being able to control and drive at least two devices, one supporting the other, in order to optimize contact with the endocardial surface. This invention is intended to address this need by disclosing methods and apparatus for navigating multiple medical devices from a single remote navigation system that actuates both devices. In the present invention, an interventional deflectable sheath device is steered and controlled by the remote navigation system either by manual operation from a user interface or in automated manner. A second medical device is passed through the deflectable sheath device and is also steered and controlled from the remote navigation system. The second medical device could be for instance a localized ablation catheter. Given a desired target location for the ablation catheter to access, and that may be selected for example from an electroanatomical map, the present invention describes methods of driving the deflectable sheath to automatically provide an optimal spatial configuration from which the ablation catheter device can access the target with good contact. Thus, both medical devices, sheath and catheter, are controlled by the remote navigation system to optimize contact.

There are at present no methods that implement such generalized control of multiple medical devices for optimal contact from a single remote navigation system. The disclosure of the present invention provides methods for achieving such objectives.

SUMMARY OF THE INVENTION

The present invention relates to methods of remotely controlling steering and navigation of multiple medical devices through a subject anatomy with an interventional remote navigation system in order to generate good quality contact with desired targeted tissue surface in the subject anatomy. According to the methods taught in the present invention, a first medical device in the form of a deflectable sheath whose deflection can be controlled from the remote navigation system is remotely steered by the remote navigation system. The remote navigation system generally configures and positions the deflectable sheath device by actuating deflection, rotation and insertion/retraction degrees of freedom. Given a desired target location that a user desires to access in a subject anatomy, the remote navigation system runs a computational model to determine an optimal configuration of the deflectable sheath device and drives its placement such that the distal tip of the sheath is aimed approximately at the target while maintaining a pre-defined distance from the target. The pre-defined distance can incorporate a safety distance as well as a margin of sufficient distance that allows the navigation and placement of a second medical device in the form of an ablation catheter that is passed through the lumen of the deflectable sheath.

The deflectable sheath device is driven by passing it though a drive mechanism (such as the Vdrive™ unit manufactured by Stereotaxis, Inc. of St. Louis, Mo.) where rotations of appropriate catheter handle regions are generated by suitable gripping/clamp mechanisms driven by drive motors. These rotations can result in rotations of the catheter shaft and deflections of the deflectable sheath distal portion generated by pull-wires inside the catheter. Likewise, catheter insertion/retraction is generated mechanically by translation of the gripping mechanisms over a length range, again driven by a suitable drive motor and appropriate motion transmission mechanisms. Further details of such drive mechanisms for remote device manipulation are disclosed in US patent application 2009/00105645, "Apparatus for selectively rotating and/or advancing an elongate device", and US patent application 2010/0298845, "Remote manipulator device", attached here for reference.

The process of automatically configuring the deflectable sheath device could be implemented based on the computational model together with positional feedback from the motors driving the configuration of the sheath device in one preferred embodiment. In an alternate preferred embodiment, the deflectable sheath can have electrodes on its distal portion that can be localized spatially with a localization system. In this latter case localization data for the tip electrodes can be used as positional feedback and the control algorithm to use feedback to adaptively drive the sheath configuration until it is actually positioned as intended. In still another preferred embodiment, the ablation catheter that passes through the lumen of the deflectable sheath is localized, for example with data from a suitable sensor placed in the distal tip of the catheter. In this embodiment, the catheter is positioned with its distal tip at or just beyond the distal tip of the deflectable sheath, and localization data (position and orientation) from the catheter device is used as input to a feedback-controlled navigation scheme to configure the deflectable sheath.

The computational model for the sheath can determine configurational degrees of freedom for the sheath in order to satisfy the constraints of pointing the distal tip of the sheath at a desired target location while maintaining a given pre-defined distance from it. These constraints are posed as a mathematical problem according to the teachings of the present invention and a solution is determined computationally. If the constraints are not satisfiable in exact manner, a "closest" solution can be determined for the sheath configuration that is as optimal as possible. For exemplary purposes, the disclosure herein treats the case of a (first) deflectable sheath device that it is desired to point at the target location to the best extent possible, while a (second) medical device in the form of a mapping/ablation catheter is passed through the lumen of the sheath. Both devices are driven from a single remote navigation system, while the steering modality generally could be different for the two devices; thus the first device (deflectable sheath) could be actuated mechanically, while the second device (ablation catheter) could be steered magnetically. The ablation catheter device can itself be steered using closed loop feedback control methods that have been disclosed previously (for example, in US Patent application number 2005/0020911, "Efficient closed loop feedback navigation"). Furthermore a range of other actuation schemes could be used, and likewise a larger multiplicity of devices could be deployed in the clinical application and controlled according to the teachings of the present invention, without departing from the scope of the present invention.

DETAILED DESCRIPTION OF THE EMBODIMENTS

The present invention describes a set of methods for automatically navigating with a remote navigation system at least one medical device in the form of a deflectable sheath together with a second medical device in the form of a magnetic navigation device, such that for a given target location in a subject anatomy, the two devices are steered by the remote navigation system for optimal access to and contact with the desired target location. In particular and for purely exemplary purposes, consider the case of the magnetic navigation device in the form of an ablation catheter that is steered with a remotely operated navigation system by application of a suitable magnetic field, while the deflectable sheath device is steered by the remote navigation system by mechanical actuation means. With the methods taught in the present invention, the remote navigation system steers and configures the deflectable sheath to aim its distal tip at the target to at least an approximate extent while maintaining a pre-defined distance margin from the target, and the ablation catheter that passes through the sheath is steered by the remote navigation system to access the target with optimal contact.

Figure 1:
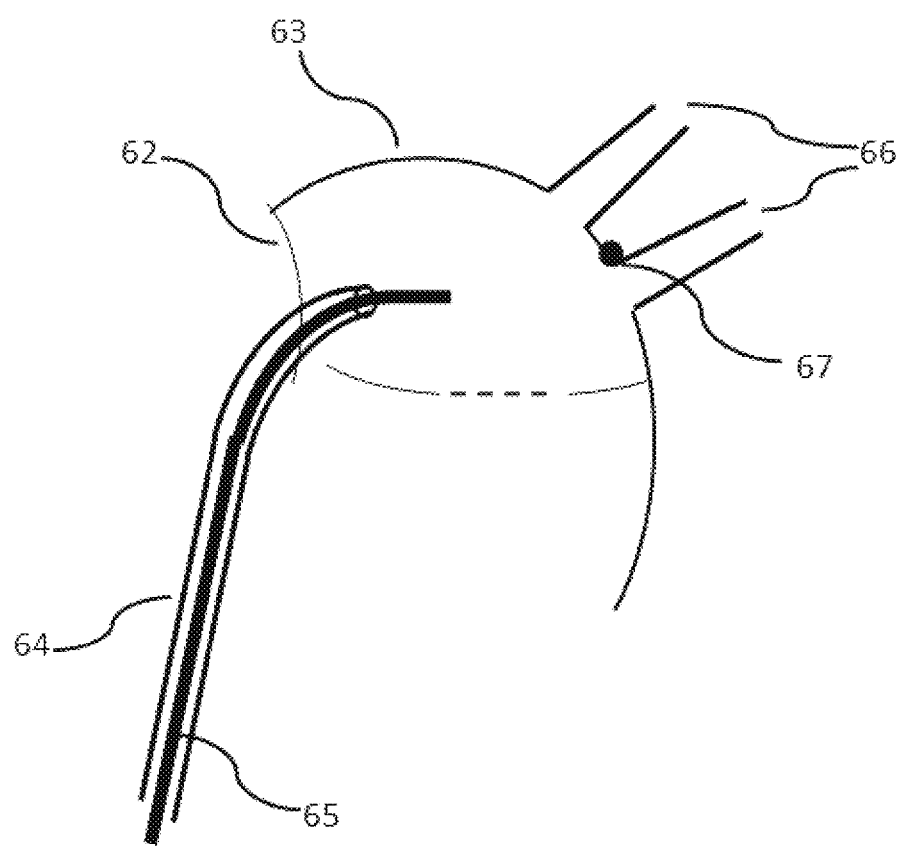
FIG. 1 is a schematic illustration of a deflectable sheath inserted in a left atrial heart chamber, showing a desired target location on the endocardial surface, and a catheter device passing through the lumen of the deflectable sheath and inserted into the left atrial heart chamber for subsequent navigation.

An exemplary application and geometrical disposition is shown schematically in FIG. 1. Referring to FIG. 1, a deflectable sheath device 64 is shown with an ablation catheter 65 passing through its lumen, and the sheath passes through the septum 62 separating right and left atrial chambers of a heart and enters the left atrium 63. Also shown in the figure are pulmonary veins 66 extending from the left atrium. A target location 67 on the endocardial surface is shown marked by a dark spot. As shown, the distal tip region of the deflectable sheath 64 is inserted into the left atrium via a trans-septal puncture. The distal tip portion the ablation catheter 65 extends beyond the tip of the deflectable sheath for further steering and navigation to access endocardial locations. The catheter 65 is used to perform an Electro-Physiology (EP) procedure where intracardiac electrograms are recorded with the catheter to diagnose arrhythmic regions of the heart and an RF ablation process is used to electrically isolate undesirable electrical nodes in the cardiac anatomy.

Figure 2:
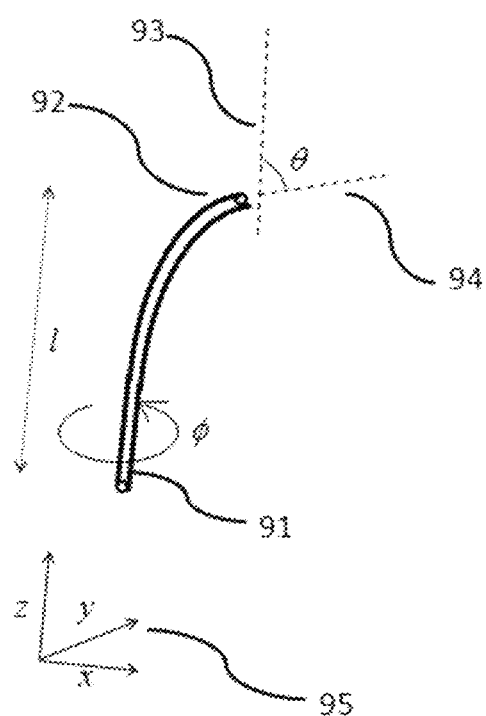
FIG. 2 is an illustration of the degrees of freedom associated with the deflectable sheath device that are used in the formulation of the computational model.

FIG. 2 illustrates the degrees of freedom associated with the deflectable sheath. The base 91 of the sheath can be moved in and out or advanced and retracted at a given location. The length of sheath beyond this location is denoted by the variable 1, and is the length degree of freedom. Further the catheter can rotate about its long axis by a rotation angle f (from some reference configuration) as shown by the circular motion indicated by the circular arrow at the base of (a portion of) the catheter in FIG. 2. The distal tip region 92 can deflect by an angle q with respect to the base, as shown by the angle between dotted lines 93 and 94 that are parallel to the base orientation and the distal tip orientation, respectively. A local frame of coordinates 95 is defined at the base of the sheath as a coordinate basis for computations.

Figure 3:
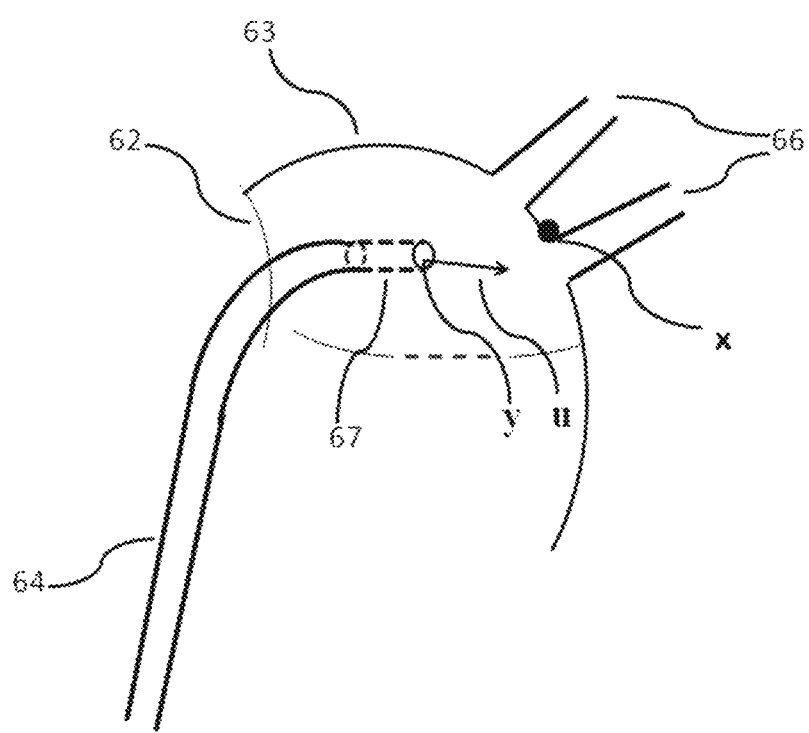
FIG. 3 shows a typical geometrical disposition of a deflectable sheath in an atrial chamber and a representative target location, and labels associated variables that are used in the automated control scheme of the present invention.

Some of the variables associated with the deflectable sheath are shown in the schematic illustration in FIG. 3. The deflectable sheath 64 enters a left atrial chamber 63 in a subject cardiac anatomy after passing through a puncture in the septal wall 62 separating right and left atria. Pulmonary veins 66 are also shown in this schematic illustration. The sheath has a rigid distal tip portion 65. A target location labeled by its three dimensional coordinates x is shown as a dark spot near the pulmonary veins. The distal tip of the sheath is labeled by its coordinates y and the unit tangent vector to the sheath at the distal tip y is labeled u.

Figure 4:
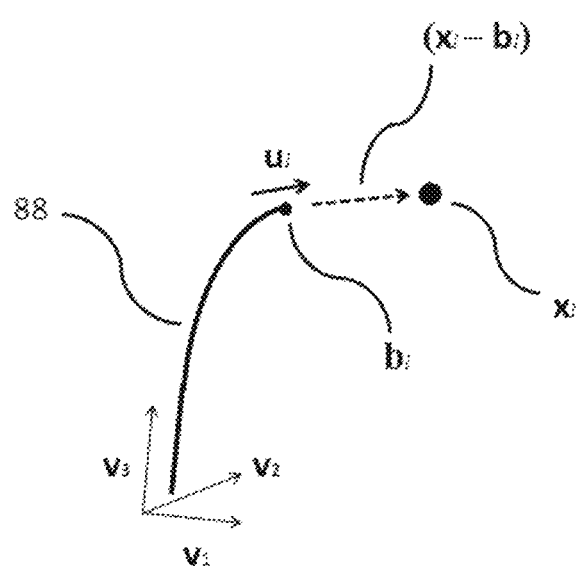
FIG. 4 is a schematic illustration of a typical geometrical configuration of the deflectable sheath in relationship to a desired target location where all the labeled variables are planar variables in the plane of deflection of the sheath.

Given a target location, the deflectable sheath may be brought (by rotation about its long axis) to a configuration where the base and tip of the sheath and the target location all lie in a single plane. In this plane, local coordinate variables can be defined and used. As shown in FIG. 4, the sheath 88 ends at distal tip labeled by $b_l$ in local coordinates and the unit tangent vector in local coordinates is labeled $b_l$. The local coordinate system is labeled by its orthonormal axes which are defined (in global coordinates) by the unit vectors $v_1$, $v_2$ and $v_3$ as shown at the base of the sheath. In this local frame, the target location has coordinates $x_l$ and the tip-to-target vector is $(x_l - b_l)$.

In practice, the deflectable sheath length that is modeled starts at a known anatomical location, for instance where the Inferior Vena Cava (IVC) enters the right atrium. For convenience, we consider the case where the entire length of sheath further to this anatomical location is deflectable, except for a rigid tip portion. If the maximum deflectable length of the deflectable sheath is L, the (deflectable) length of sheath l inserted in the right atrium and that we will model usually satisfies l<L. As will be described in the following, a calibration procedure is followed for the deflectable sheath before automated steering of the sheath is invoked. The deflectable sheath is driven by passing it though a drive mechanism (such as the Vdrive™ unit manufactured by Stereotaxis, Inc. of St. Louis, Mo.) where rotations of appropriate sheath handle regions are generated by suitable gripping/clamp mechanisms driven by drive motors. These rotations can result in rotations of the sheath shaft and deflections of the sheath distal portion generated by pull-wires inside the sheath. Likewise, sheath insertion/retraction is generated mechanically by translation of the gripping mechanisms over a length range, again driven by a suitable drive motor and appropriate motion transmission mechanisms. Further details of such drive mechanisms for remote device manipulation are disclosed in US patent application 2009/00105645, "Apparatus for selectively rotating and/or advancing an elongate device", and US patent application 2010/0298845, "Remote manipulator device", attached here for reference.

Figure 6:
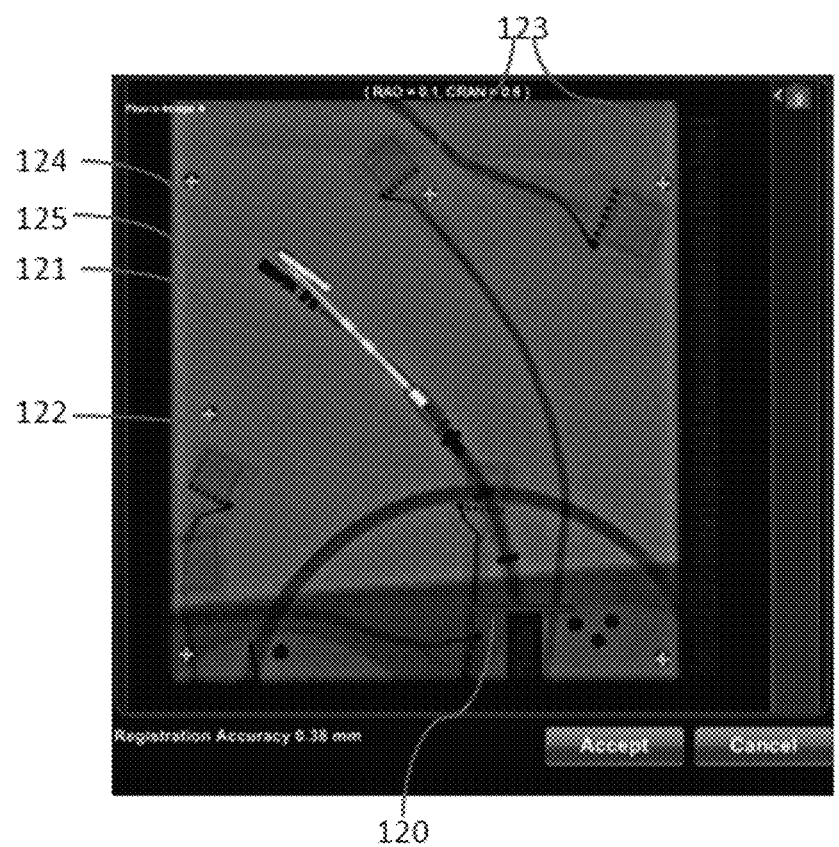
FIG. 6 shows a portion of a user interface of the present invention where a registration and calibration procedure is performed for the deflectable sheath with an X-ray image. A localized ablation catheter passes through the sheath and its localized distal tip is graphically rendered in the X-ray view in the user interface. The user marks a length of catheter that extends from the sheath together with a crossing plane perpendicular to the sheath that marks an approximate entry location (into a heart chamber) and orientation direction for the sheath. The base of the marked catheter length serves to indicate an initial extended length for the sheath, and the orientation of the catheter provides information for an estimate of the spatial disposition of the initial plane of deflection of the sheath

In a preferred embodiment, the deflectable sheath can itself be a localized device (for instance by means of localizing electrodes mounted in its distal tip region), and the position and orientation of the tip are known quantities. In an alternate preferred embodiment, the sheath when used with a localized catheter can have its distal tip localized by placing the distal tip of the ablation catheter at or near the distal tip of the sheath. The deflectable sheath's base orientation is also assumed known (for instance, it may be assumed to be along the z axis in the case where it enters the right atrial chamber along the IVC). Further, the calibration process allows the user to identify the sheath distal tip at or near the point of entry into the chamber, which defines a reference position for the length of the catheter. Specifically, referring to FIG. 6, this figure shows an X-ray image displayed on a portion of a graphical user interface of the remote navigation system along with various overlays. The crossing plane 120 of the sheath is a user-marked plane at a user-defined location of entry of the sheath into an anatomical region. For example, this could be an entry point associated with entering a right atrial cardiac chamber. The X-ray image shows the deflectable sheath 122 together with an ablation catheter 125 extending out from the sheath. Also seen in the figure are markers 123 associated with a localization system interfaced with the remote navigation system that localizes the ablation catheter (and the sheath if the sheath is endowed with electrodes). The markers 123 serve to register the localization system with the remote navigation system via an X-ray system that also interfaces with the remote navigation system. Initially the user deflects the sheath by a relatively small amount (for example, around 25-30 degrees) by manual operation of a user interface to deflect the sheath. The user marks the catheter by means of graphical representation 121 (drawn as an overlay by dragging a computer mouse in the user interface display), drawn approximately from distal tip of the catheter (as seen on the X-ray image) to the distal tip of the sheath (from which the catheter emerges).

With this latter information about the position and orientation of the distal tip of the sheath, and with the known data for the location and orientation of entry of the sheath base, the remote navigation system can compute the initial deflection plane of the sheath. Subsequent deflection plane orientations can be computed using the (localized) orientation of the catheter and the sheath base orientation; alternatively, the deflection plane can be kept track of by tracking motor movements that serve to rotate the sheath. Specifically, since the catheter tip is localized, an initial reference position for the rotation angle f (f=0) is also defined and subsequent (values can be determined from tip orientation and the known base direction. Likewise, from the known sheath tip orientation the reference deflection angle q is also known. The current (initial) motor positions (determined from appropriate encoders) for the device manipulation drive mechanism for the respective degrees of freedom can also be recorded as reference values.

Figure 5:
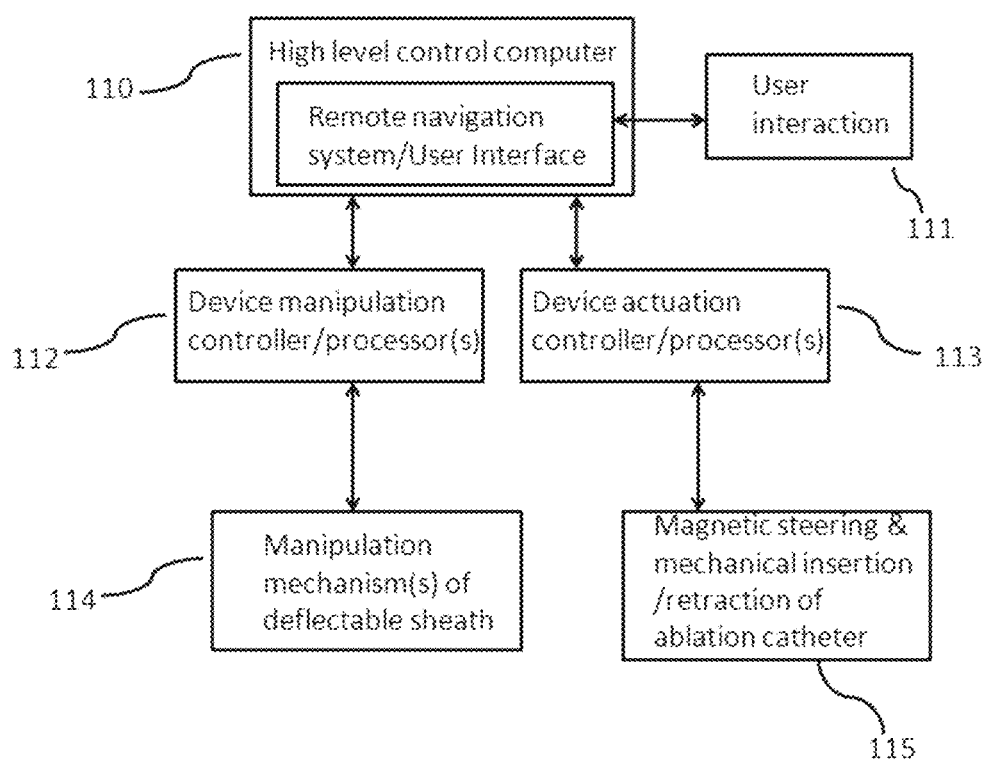
FIG. 5 is a schematic depiction of a system diagram of the present invention illustrating various system components and communication paths.

FIG. 5 is a high-level system diagram describing one version of a system architecture for implementing the teachings of the present disclosure. The remote navigation system has a high level control computer 110 that runs, among others, the remote navigation user interface which offers user interaction 111 permitting a user to view various displays and operate an assortment of controls. Some of these control inputs generally conceivable as user interaction means 111 could be, additionally to graphical user interface tools such as buttons, sliders, clicking on various visual displays, etc., in the form of hardware such as a mouse, joystick, or other input devices with a combination of joystick and buttons. Such input devices and user interaction means are known widely in the prior art and are not described in detail here. The high level control computer 110 of the remote navigation system interfaces with a device manipulation controller or controllers 112, and with a set of device actuation controllers/processors 113, respectively to manipulate or generally actuate a deflectable sheath, and a magnetic ablation catheter. The device manipulation controller(s) 112 drive (servo) motors in a manipulation mechanism 114 which controls and drives the handle of the deflectable sheath, and which can generally rotate, deflect, or advance/retract the sheath. Encoders in the motors keep the manipulation controller(s) appraised of motor positions and/or velocities etc. Likewise the device actuation controllers/processors 113 drive motors associated with moving magnets to create an appropriately directed magnetic field to steer the ablation catheter device, as well as a motor to advance or retract the ablation catheter, all represented as steering and insertion/retraction operations 115. Both devices in some cases (deflectable sheath and ablation catheter), or either device, could be localized and their localization information is available to the high level control computer 110 of the remote navigation system via interfacing to a localization system (not shown). Thus the single high level control computer 110 has access to all the relevant information needed to steer the deflectable sheath as well as the catheter device suitably in order to access targets optimally.

The deflectable generally has a rigid tip of known length t (for instance, t can be in the approximate range of 1-2 cm). Further, we make the assumption that the deflectable portion of the sheath has uniform physical properties. In this case, the deflection of the sheath that is generated by tension in a pull-wire within it follows a circular arc. If a deflectable length of sheath l extends from the base, and the distal sheath tip is deflected by an angle q relative to the base, the tip location y can then be written in local coordinates (in the coordinate frame shown in FIG. 2, with the base of the catheter as origin) explicitly in terms of components as $$y_l = \left(\frac{l}{\theta}(1-\cos\theta)\cos\phi, \frac{l}{\theta}(1-\cos\theta)\sin\phi, \frac{l}{\theta}\sin\theta\right) + \quad (1)$$

$$t(\sin\theta\cos\phi, \sin\theta\sin\phi, \cos\theta)$$

In general, we would like to also maintain a margin of adjustment in terms of distance from the distal tip of the sheath to a given target location. Thus, we define a total distance d as the sum of rigid tip length of the sheath and a margin-of-adjustment distance. The margin of adjustment distance serves both as a safety buffer zone so that the sheath stays sufficiently away from the endocardial wall, and so that there is sufficient length for the ablation catheter (which extends from the sheath tip) to maneuver as needed and access a target. In a preferred embodiment, the total distance d can be in the range 1-6 cm. Given a target x, we would then like the distal end of the deflectable portion of the sheath to be maintained at a distance d from target x, while pointing directly at the target. In the following we provide a computational solution of this problem.

Let (unit vector) $v_3$ be the direction of entry of the sheath, and let p be the location of entry or the base of the sheath. Define $v'_2=v_3\times(x-p)$ and the unit vector $v_2=v'_2/|v'_2|$. Also define $v_1=v_2\times v_3$. Then $(v_1, v_2, v_3)$ define an orthornormal set of basis vectors at the sheath base. Let b be the location of the distal end of the deflectable portion of the sheath length (at the base of its rigid distal tip). Define the quantity $a=(b-p)\cdot v_3/|b-p|$ and let $b'=(b-av_3)/|b-av_3|$. Let $f=\cos^{-1}(b'\cdot v_1)$ and let $e=\text{sign}[(b'\times v_1)\cdot v_3]$. Now if the sheath is rotated by the angle $(-ef)$ counterclockwise about the long axis $v_3$, it will lie in the plane defined by the vectors $v_3$ and $(x-p)$. Accordingly, this is the first step in the computation of steering requirements: a rotation of the sheath is found as described in the above that ensures that the target x lies in the deflection plane of the sheath.

Now suppose that a length l of sheath is extended from the sheath base. After the rotation defined above, the curve of the sheath lies in the $(v_1, v_3)$ plane. Let the sheath be deflected by an angle q (measured in radians). Given the circular arc defined by the curve of the sheath, the location $b_l$ of the distal end of the deflectable portion of the sheath length can be written in local coordinates (attached to the orthonormal set $(v_1, v_2, v_3)$) as $$b_l = \left(\frac{l}{\theta}(1-\cos\theta), 0, \frac{l}{\theta}\sin\theta\right) \quad (2)$$

Furthermore, the target location x written in terms of the same local coordinates as $x_l$ has only non-zero components $x_1\equiv(x\cdot v_1)$ and $x_3\equiv(x\cdot v_3)$ along local axes $v_1$ and $v_3$ respectively. In these local coordinates, the unit tangent vector at the distal end $b_l$ of the deflectable portion of the sheath can be written as $$u_l=(\sin q, 0, \cos q) \quad (3)$$

Since we would like the distal end $b_l$ of the deflectable portion of the sheath to be aimed directly at the target $x_l$, we can write this alignment constraint mathematically as $$x_l-b_l=ku_l \quad (4)$$

where k is a positive constant. From equations (2) and (3) above, we can re-write equation (4) in terms of its components:

$$x_1 - \frac{l}{\theta}(1-\cos\theta) = k\sin q \quad (5)$$

$$x_3 - \frac{l}{\theta}\sin\theta = k\cos q$$

Dividing these equations yields the equation $$\frac{l}{\theta}(1-\cos\theta) = x_3\sin\theta - x_1\cos\theta \quad (6)$$

Further, the distance constraint that the distal end of the deflectable portion of the sheath be positioned at a distance d from $x_l$ can be written in the form $$|x_l-b_l|^2=d^2$$

or in terms of components $$\left(x_1-\frac{l}{\theta}(1-\cos\theta)\right)^2 + \left(x_3-\frac{l}{\theta}\sin\theta\right)^2 = d^2 \quad (7)$$

For a given value of deflection angle q equation (7) may be solved for length l from a quadratic equation. Specifically, defining the quantities $$B \equiv \frac{\theta}{(1-\cos\theta)}[x_1(1-\cos\theta) + x_3\sin\theta] \quad (8)$$

$$C \equiv \frac{\theta^2}{2(1-\cos\theta)}(x_1^2 + x_3^2 - d^2)$$

equation (7) can be written as a quadratic equation for l:

$$l^2-Bl+C=0$$

with solutions given by $$l=\frac{1}{2}(B\pm(B-4C)^{1/2}) \quad (9)$$

Real solutions to equation (9) exist only when $B\geq 4C$.

Thus, one method of finding a solution is to do a search over a range of discrete values of q (say in the range $0\leq\theta\leq 3\pi/4$), find solution(s) for length values l from equation (9), and check to see whether the alignment equation (6) is satisfied, with a further check to ensure that k in equation (4) is positive:

$$\left(x_1-\frac{l}{\theta}(1-\cos\theta)\right)\sin\theta > 0 \quad (10)$$

Since there are generally multiple (two) solutions for the length l from equation (9), we would need to check both solutions for alignment from equations (6) and (10).

In some cases there may not be an exact solution from equations (6) and (10) for aligning the sheath tip with the target. In this case, the alignment constraint equation (4) can be "opened up" and one can look for solutions such that $(x_l-b_l)$ and $u_l$ are aligned to within some pre-determined angular range, for example to within 30 degrees, and these could still be acceptable solutions. In some cases it may also be useful to check whether acceptable solutions for the sheath length l exist within the range of the actual upper bound L of deflectable sheath length.

Once a solution for the sheath configuration is found, the sheath can be suitably steered and configured by the remote navigation system based on the values of q and l determined as solutions to the targeting problem. For example the mechanical motor-driven drive system mentioned earlier can be used to effect this automated steering of the sheath. By pointing the sheath distal tip at the desired target and maintaining a relatively short distance from the target, the length of ablation catheter that needs to be extended out from the sheath is kept minimal. Furthermore the target can be directly accessed with relatively small fine adjustments to the catheter position which can be easily driven by magnetic actuation from the remote navigation system. As described in prior art, since the catheter is localized it can also be automatically steered and adjusted by the remote navigation system under closed-loop feedback guidance. Since the length of catheter needed to access the target in this mode of operation is minimal, and since the contact force exerted by the catheter tip at the endocardial surface can be shown to be approximately inversely proportional to the catheter length to leading order, this also means that a good level of contact force can be exerted by the catheter at the tissue surface and good contact can be maintained.

Figure 7:
FIG. 7 shows a portion of a user interface of the present invention where a localized ablation catheter distal tip is displayed on an X-ray image acquired in the calibration step and where the ablation catheter has been retracted compared to its initial position. The predicted sheath configuration based on a computational model used to model the sheath configuration is also displayed as an overlay on the X-ray image in the form of a dotted curve. The plane of deflection for the sheath as estimated from the calibration step and the catheter orientation provides the extent of deflection; these quantities are used as input to the computational sheath model.

FIG. 7 shows a portion of a user interface of the present invention where the ablation catheter distal tip is graphically rendered as an overlay on an X-ray image. After the initial calibration step described previously, the computational model reconstructs a modeled sheath configuration indicated by the dotted curve 131 overlaid on the X-ray image. The modeled sheath curve can be seen to conform quite closely to the actual sheath curve 130 seen in the X-ray image. The catheter has been positioned so that its distal tip portion 133 extends just beyond the sheath distal tip 132. Also shown is a low-field magnetic field vector 134 in green corresponding to magnetic actuation that has not yet been applied in the navigation volume.

Figure 8:
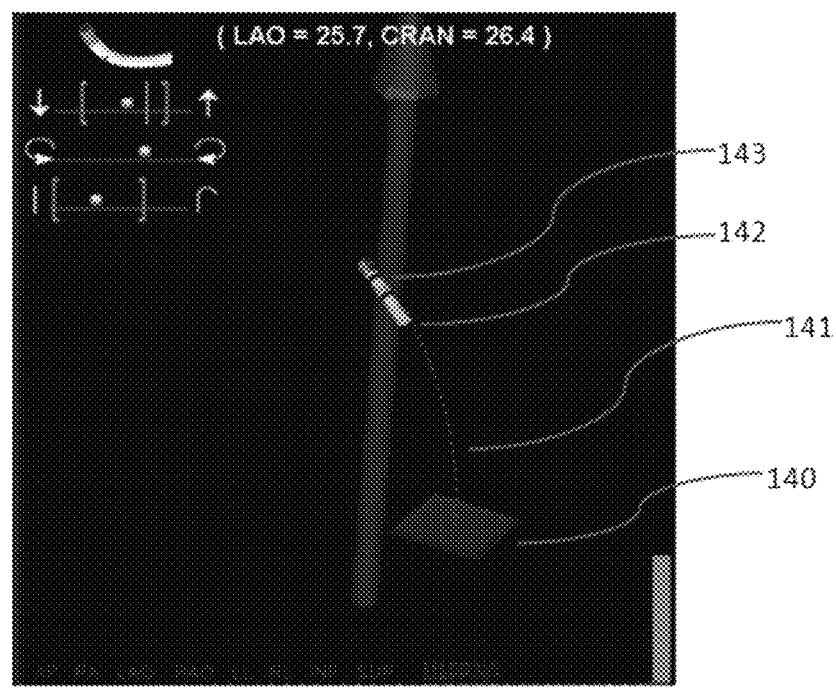
FIG. 8 shows a portion of a user interface of the present invention where a graphical display is provided of a three dimensional scene showing the crossing plane of the sheath and a localized ablation catheter tip retracted until it is just beyond the distal end of the deflectable sheath. The computational model of the sheath is used to generate a predicted sheath configuration that is graphically rendered in the three dimensional scene as a dotted curve.

FIG. 8 shows a three dimensional scene from a graphic display that is part of a user interface of the present invention. A modeled sheath curve configuration 141 is shown extending from crossing plane 140 corresponding to the base of the sheath. A localized ablation catheter 143 extends from the distal tip region 142 of the deflectable sheath and can be seen to be closely correspond in location to the expected location as the catheter extends beyond the sheath.

Figure 9:
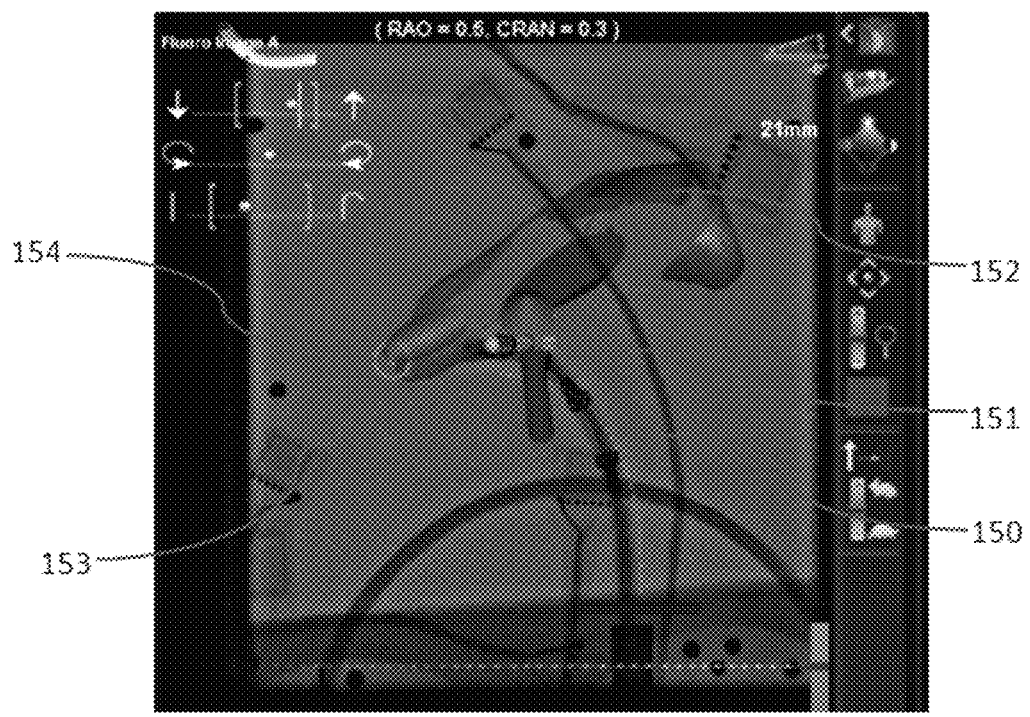
FIG. 9 shows a portion of a user interface of the present invention where a portion of an electroanatomical map representing a cardiac surface is displayed on an X-ray image, together with a user-selected target on the map. In response to the target selection, the remote navigation system steers the deflectable sheath to a configuration that points to the target. A localized ablation catheter distal tip is also displayed on the X-ray image and is shown in the figure approaching the target.

FIG. 9 shows a portion of a user interface of the present invention where an electroanatomical map 152 is overlaid on an X-ray image. The user has selected a target location 154 on the map. The computational model of the present invention generates and steers a sheath configuration as shown by dotted curve 150 also overlaid on the X-ray image, so as to point the sheath towards the target location. The localized distal tip 151 of the ablation catheter is seen to extend out from near the distal tip 152 of the sheath curve.

Figure 10:
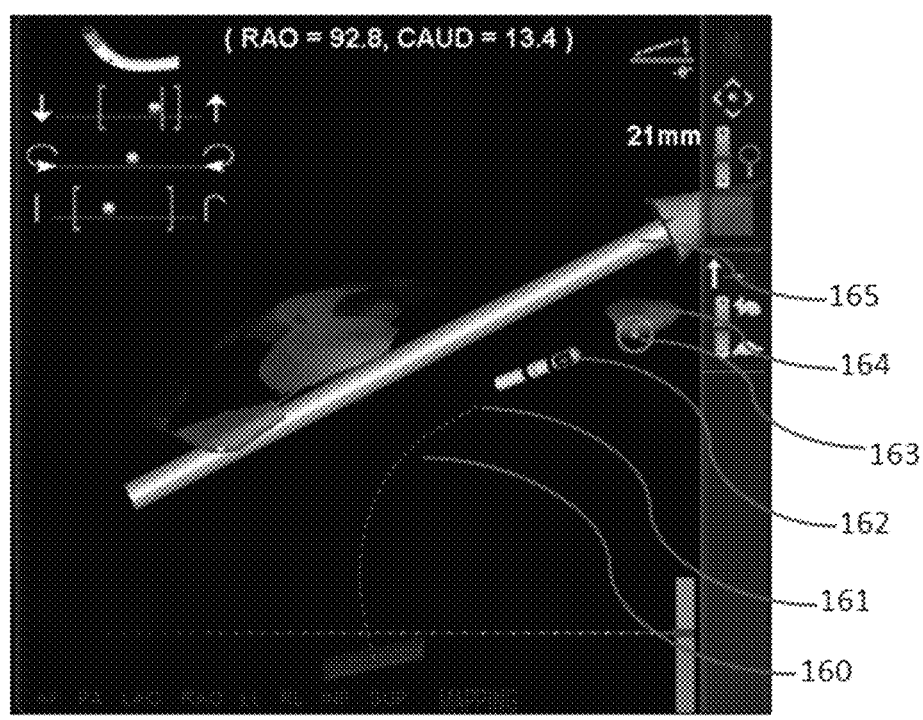
FIG. 10 shows a portion of a user interface of the present invention where a graphical display is provided of a three dimensional scene displaying a portion of an electroanatomical map representing a cardiac surface, together with a user-selected target on the map. In response to the target selection, the remote navigation system steers the deflectable sheath to a configuration that points to the target. A localized ablation catheter distal tip is also displayed on the X-ray image and is shown in the figure approaching the target. The ablation catheter is also steered by the remote navigation system using magnetic navigation and application of an appropriate magnetic field.

FIG. 10 shows a three dimensional scene from a graphic display that is part of a user interface of the present invention where a target location 163 has been selected by a user on a portion 164 of an electroanatomical map. The computational model of the present invention is used by the remote navigation system to steer the sheath to a modeled configuration indicated by dotted curve 160 with its distal tip 161 pointed at the target. The remote navigation system applies a magnetic field vector 165 that is aligned with the tangent direction at the sheath distal tip. The actual localized distal tip 162 of the ablation catheter can be seen to be approaching the target location 163, demonstrating operation of the present invention.

In one embodiment the current configuration's degrees of freedom (q, l and f) can be estimated from knowledge of the (localized) current ablation catheter tip position (positioned near the distal tip of the sheath) and the known base entry position p, and fitting the degrees of freedom from equations (2) and (3) to determine them. In an alternate embodiment, an internal map is maintained between appropriate drive mechanism motor positions and the corresponding degrees of freedom (for example and for illustration purposes only, a 90-degree turn of an appropriate motor shaft may correspond to a 25-degree deflection in the distal sheath tip, etc.), and this map is used together with knowledge of current motor positions or related drive mechanism variables to estimate a current set of values for the sheath degrees of freedom. In yet another alternate embodiment, a combination of these two methods could be used to find a best-fit estimate of the sheath degrees of freedom.

In some cases the change in degrees of freedom that actually occur upon steering by the remote navigation system may not correspond exactly to the desired values applied. This can occur for example due to anatomical obstructions or due to hysteresis effects in the drive system that actuates the deflectable sheath. In order to compensate for such effects, feedback control techniques can be implemented. In one preferred embodiment of the present invention, as a first step in steering the sheath the computational model of the present invention is invoked and an initial sheath configuration is applied from the computationally determined degrees of freedom. In a second step applied immediately after the first step, adjustments are applied to the rotation and deflection angles (f and q respectively) as follows:

$$\delta f = m_1 f_0$$

$$\delta \theta = m_2 \theta_0 \quad (11)$$

where $m_1$ and $m_2$ are appropriate gain constants such that $0 < m_1 < 1$ and $0 < m_2 < 1$. Here $f_0$ is a deficit rotation angle that is computed from the current sheath distal tip location information (determined either from sheath tip localization, if available, or from placement of the localized ablation catheter distal tip near the sheath tip) and target location as described in paragraph 32 above. Likewise $\theta_0$ is a deficit deflection angle that is computed from distal sheath tip orientation (again determined either from sheath tip localization, if available, or from placement of the localized ablation catheter distal tip near the sheath tip), and tip-to-target orientation; this is computed as the angular difference between these orientations after the deficit rotation by angle $f_0$ is computationally applied. This process may be iterated until the deficit angles become sufficiently small, or the process can run for a fixed, pre-defined number of steps and then stop.

While the above control scheme describes a proportional control methodology, more general feedback control schemes known in the art such as for instance Proportional-Integral-Derivative (PID) control schemes can also be implemented. Alternatively, a state vector-based scheme could be implemented. For example, defining the unit vector $q = (x-b)/|x-b|$, one can define the error measures $e_1 = v_2 \cdot u$ and $e_2 = v_3 \cdot u - (v_3 \cdot q)(u \cdot q)$. We can define the state vector $v = [f \; q]^T$, the control vector $u = [Df Dq]^T$ and the output function $e = h(v)$. If k is the control update count, we can write the update rule $$\begin{aligned} v(k+1) &= v(k) + u(k) \\ e(k+1) &= h(v(k+1)) \\ &\cong h(v(k)) + \frac{\partial h}{\partial v}(v(k))u(k) \\ &= h(v(k)) + A(k)u(k) \end{aligned} \quad (12)$$

where A(k) may be computed by finite differences or analytically.

Assuming that A is invertible, the feedback law can be written $$u(k) = A^{-1}(k)Ke(k) \quad (13)$$

with $$K = \begin{pmatrix} k_1 & 0 \\ 0 & k_2 \end{pmatrix}.$$

The closed loop dynamics become $$e(k+1) = (I+K)e(k) \quad (14)$$

or in component form, $$e_1(k+1) = (1+k_1)e_1(k)$$

$$e_2(k+1) = (1+k_2)e_2(k)$$

The process is generally iterated until the error vector e becomes suitably small. The quantities $k_1$ and $k_2$ are chosen such that $0<(1+k_i)<1$. As $(1+k_i)$ gets smaller, the response gets faster, but must be chosen so that oscillations do not occur.

To summarize, the process of finding an optimal solution can proceed as follows. We will treat the target position as given and vary the sheath degrees of freedom to find a solution where the sheath is steered and moves into a configuration where its distal tip is aimed directly at the target as much as possible. This is done first with a computational model for the sheath whereby an initial steering of sheath configuration is computed by solution of equations (6) and (9) as described in the foregoing and implemented by the remote navigation system by mechanically driving the deflecting sheath degrees of freedom suitably. Subsequently, closed-loop feedback for further adjustment of the sheath can be implemented by any of a variety of methods as described above in detail until an optimal configuration is reached to the extent possible. At this point the sheath is optimally positioned for the catheter to access the target. Next the (localized) catheter is extended out sufficiently from the sheath, and magnetic actuation of the catheter is applied from the remote navigation system so as to apply a suitable magnetic field vector to make adjustments to the ablation catheter tip position along with suitable insertion/retraction of the catheter (also generally applied by the remote navigation system) until it arrives at the target. Thus, a single remote navigation system can control and steer multiple devices as taught in this invention so as to optimally access target locations in a subject anatomy.

The steering of the sheath can be automatically invoked from a user interface of the remote navigation system by any of a variety of means, for example by clicking on a suitable icon on the graphical user interface, from a button on a joystick or other controller, etc. In one preferred embodiment, the iterative changes in the degrees of freedom are continuously operational as long as the automated tracking mode is engaged. In an alternate preferred embodiment, the iterative applications of changes in the degrees of freedom are stopped once the respective changes become small enough quantities that lie below pre-defined threshold values, and automatically resume once they start growing again due to selection of a new target. In this manner, the remote navigation system becomes easy to use for the user/physician, and automatic targeting can permit good access to a variety of desired anatomical sites and with minimal user interaction.

The advantages of the embodiments described here in detail and improvements thereupon should be readily apparent to one skilled in the art, for purposes of providing a fast and effective set of automated control algorithms for the steering, control and positioning of multiple medical devices by a single remote navigation system. The various automated positioning schemes described in the present invention permit actuation and steering of multiple medical devices generally in automatic fashion using device location information. Furthermore, while the specific description in this disclosure has discussed in detail the case where a deflectable sheath is mechanically steered and the ablation catheter is generally steered by magnetic navigation means, it should be obvious to one skilled in the art that a variety of other combinations of actuation schemes could also be implemented without departing from the spirit and scope of the present invention. The general approach disclosed in the present invention is that geometric constraints for target access can be encoded in suitable computational and control algorithms that can be implemented with a remote navigation system to steer and configure multiple medical devices for optimal target access.

While one of the devices in the description given in the present disclosure is a magnetic ablation catheter driven that is generally steered by a magnetic navigation system, the methods of the present invention can be extended to other actuation schemes. Thus, the method of actuation used by the remote navigation system can be any of a variety of actuation methodologies known in the art, including without limitation magnetic navigation methods, mechanical actuation, electrostrictive actuation, hydraulic actuation, etc. The remote navigation system may also use a combination of actuation modalities so that in some embodiments, multiple actuation schemes may be used by the remote navigation system. In one embodiment, the same device can be actuated with different actuation modalities; for example, a magnetic catheter can be mechanically advanced and magnetically deflected or steered. For convenience, the term "remote navigation system" in the description herein refers without limitation to any system that uses such remote actuation techniques or modalities singly or in combination, and the automated positioning algorithms of the present invention can drive or navigate devices that employ any or a multiplicity of such actuation methods.

Generally, the methods of the present invention apply to the automatic steering and control of a multiplicity of remotely navigated or steered medical devices. A single high-level control computer that is part of the remote navigation system runs navigation algorithms designed to automate this coordinated movement and/or positioning of multiple devices. A combination of different actuation schemes may be used at the same time to control or actuate different medical devices, or even different types of movements of a single device, as may be convenient for a particular application or set of applications. Additional design considerations and/or variations that are conceived by one skilled in the art may be incorporated without departing from the spirit and scope of the invention. Accordingly, it is intended that the invention is not limited by the particular embodiments or forms described above, but rather by the scope of the appended claims.

What is claimed is:

1. A method for automatically actuating and positioning a deflectable sheath device in a subject anatomy with a remote medical navigation system together with a localized second medical device that passes through the deflectable sheath device and is also actuated by the remote medical navigation system to access a desired target location, the method comprising the steps of:

(a) calibrating an initial configuration of the deflectable sheath device by manual adjustment of controls of the remote medical navigation system such that sheath deflection is generated and is visually apparent in an X-ray image, and marking on a graphical user interface a length of the second medical device near the distal tip of the deflectable sheath device, (b) selecting a desired target location in the subject anatomy to access with the second medical device, (c) computationally determining a set of degrees of freedom for optimal device configuration of the deflectable sheath device based on a computational model of device deformation and a set of geometrical constraints, (d) automatically steering the deflectable sheath device with the remote medical navigation system to the computationally determined set of degrees of freedom, (e) using position and orientation information from at least one of the deflectable sheath device or the second medical device to make automatic feedback controlled adjustments to the configuration of the deflectable sheath device, (f) repeatedly iterating the feedback-controlled adjustments to the device configuration of the deflectable sheath device until a pre-determined criterion is reached, and (g) steering the second medical device with the remote medical navigation system to access the desired target location.

2. The method of claim 1, where steps (b) through (g) are repeatedly applied as different anatomical target locations are selected.

3. The method of claim 1, where the second medical device is a magnetic ablation catheter.

4. The method of claim 1, where the step of steering the second medical device is based on generating changes to device actuation variables based on a computational model of the second medical device.

5. The method of claim 1, where the method of actuation of the deflectable sheath device comprises the change of at least one mechanically driven variable.

6. The method of claim 1, where the method of actuation of the second medical device comprises the change of a magnetic field variable.

7. The method of claim 1, where the computational determination of the set of degrees of freedom includes the satisfaction of at least one geometrical constraint involving a distance measure to the desired target location.

8. The method of claim 1, where the computational determination of a set of degrees of freedom for desired optimal desired device configuration comprises computing updates to at least one of (i) deflection, (ii) rotation, or (iii) length degrees of freedom.

9. The method of claim 1, where the computational determination of the set of degrees of freedom includes the satisfaction of at least one geometrical constraint involving distal tip alignment with the desired target location.

10. The method of claim 1, where the step of steering the second medical device is based on generating changes to device actuation variables based on a computational model of the second medical device.

* * * * *